United States Patent
Borenstein

(10) Patent No.: US 8,589,107 B2
(45) Date of Patent: *Nov. 19, 2013

(54) MEASUREMENT INSTRUMENT AND METHOD

(75) Inventor: Michael Borenstein, Boulder, CO (US)

(73) Assignee: Brooks Automation, Inc., Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/487,018

(22) Filed: Jun. 1, 2012

(65) Prior Publication Data

US 2012/0239307 A1    Sep. 20, 2012

Related U.S. Application Data

(63) Continuation of application No. 11/739,986, filed on Apr. 25, 2007, now Pat. No. 8,195,418.

(51) Int. Cl.
*G01D 1/10* (2006.01)
*G01D 1/14* (2006.01)
*G01L 7/02* (2006.01)
*G06F 3/01* (2006.01)

(52) U.S. Cl.
USPC ............. 702/104; 702/98; 702/105; 702/179

(58) Field of Classification Search
USPC ......... 702/19, 45, 79, 98, 104, 122, 138, 179, 702/191; 73/861.04; 324/142
See application file for complete search history.

(56) References Cited

U.S. PATENT DOCUMENTS

| | | | |
|---|---|---|---|
| 3,750,151 A | 7/1973 | Dill | |
| 4,949,274 A * | 8/1990 | Hollander et al. | 324/142 |
| 6,085,156 A | 7/2000 | Rust et al. | |
| 6,318,183 B1 | 11/2001 | Czarnocki | |
| 6,655,221 B1 * | 12/2003 | Aspelund et al. | 73/861.04 |
| 6,963,817 B2 * | 11/2005 | Ito et al. | 702/138 |
| 7,007,551 B2 | 3/2006 | Zdeblick et al. | |
| 7,490,512 B2 | 2/2009 | Fraden | |
| 8,195,418 B2 * | 6/2012 | Borenstein | 702/104 |
| 2006/0050464 A1 | 3/2006 | Von Arx et al. | |

FOREIGN PATENT DOCUMENTS

| | | |
|---|---|---|
| JP | 2007209122 | 8/1995 |
| JP | 2003021566 | 1/2003 |

* cited by examiner

*Primary Examiner* — Marc Armand
*Assistant Examiner* — Felix Suarez
(74) *Attorney, Agent, or Firm* — Perman & Green, LLP; Colin C. Durham

(57) ABSTRACT

A measurement instrument having a processor, a first sensor and a second sensor. The processor is adapted to output a measurement signal embodying a measurement of a physical quantity. The first sensor and second sensor are connected to the processor and are operable to generate respectively first and second measurements of the physical quantity. The processor defines a first measurement range within which the measurement signal is dependent on the first measurement and not the second measurement. The processor defines a second measurement range within which the measurement signal is dependent on the second measurement and not the first measurement. The first and second ranges meet at a predetermined transition. The first and second measurements are different at the transition and the measurement embodied in the measurement signal crosses the transition without an abrupt change.

20 Claims, 7 Drawing Sheets

MEASUREMENT INSTRUMENT AND METHOD

CROSS-REFERENCE TO RELATED APPLICATIONS

This application is a continuation of and claims the benefit of U.S. patent application Ser. No. 11/739,986 filed on Apr. 25, 2007, now U.S. Pat. No. 8,195,418, the disclosure of which is incorporated herein by reference in its entirety.

BACKGROUND

1. Field of the Exemplary Embodiments

The exemplary embodiments disclosed herein relate to measurement instruments and, more particularly, to measurement instruments having multiple sensors.

2. Brief Description of Related Developments

Many different types of sensors have been used to measure various physical quantities, for example pressure or density of a gas. As different types of sensors may have different operating ranges, it has been desired to combine different types of sensors into a single pressure instrument, with an extended operating range. For example, as the pressure of a gas is pumped down to vacuum, the output of the instrument may first correspond to a reading from one of the sensors. Then, when the output reaches a threshold value, the output may be switched to correspond to a reading from another sensor having better accuracy at the lower pressures. While this type of arrangement has an advantage in extending the pressure or density range over which the instrument can operate with suitable accuracy, there are also drawbacks. Most notably, a problem may arise in switching between the two sensors. If the two sensors do not produce identical readings at the threshold value, there may be an abrupt change in the output of the instrument when the instrument switches between sensors. Even if the difference in readings between the two sensors is small, the abrupt change can cause undesirable hysteresis effects. For example, problems may arise if the output is used as part of a feedback loop designed to control pressure. The difficulties may be more pronounced if a derivative of the output is used as a feedback signal in a feedback loop, because the derivative will be very high at the transition threshold. Therefore it may be desired to provide a pressure instrument that combine readings from two or more sensors and allow for smooth transitioning between the readings.

SUMMARY

In one exemplary embodiment, a measurement instrument having a processor, a first sensor and a second sensor is provided. The processor is adapted to output a measurement signal embodying a measurement of a physical quantity. The first sensor and second sensor are connected to the processor and are operable to generate respectively first and second measurements of the physical quantity. The processor defines a first measurement range within which the measurement signal is dependent on the first measurement and not the second measurement. The processor defines a second measurement range within which the measurement signal is dependent on the second measurement and not the first measurement. The first and second ranges meet at a predetermined transition. The first and second measurements are different at the transition and the measurement embodied in the measurement signal crosses the transition without an abrupt change.

In another exemplary embodiment, a pressure gauge comprises a pressure indicator. A first pressure sensor is connected to the pressure indicator and is operable to generate a first pressure reading. A second pressure sensor is connected to the pressure indicator and is operable to generate a second pressure reading. The pressure indicator is configured to indicate pressure responsively to the first pressure reading, without being responsive to the second pressure reading, when the first pressure reading is above a predetermined pressure threshold and falling. The pressure indicator is configured to indicate pressure responsively to the second pressure reading, without being responsive to the first pressure reading, when the first pressure reading is below the predetermined pressure threshold and falling. The pressure indicator is configured to indicate pressure as a continuous function over an indicated pressure range that includes the threshold pressure, with the second pressure reading being different from the first pressure reading when the first pressure reading is substantially equal to the predetermined pressure threshold.

In still another exemplary embodiment, a pressure gauge comprises a pressure indicator. A first pressure sensor is connected to the pressure indicator and operable to generate a first pressure reading. A second pressure sensor is connected to the pressure indicator and is operable to generate a second pressure reading. The pressure indicator is configured to indicate pressure responsively to the first pressure reading, without being responsive to the second pressure reading, when the first pressure reading is below a predetermined threshold pressure and rising. The pressure indicator is configured to indicate pressure responsively to the second pressure reading, without being responsive to the first pressure reading, when the first pressure reading is above the predetermined threshold and rising. The pressure indicator is configured to indicate pressure as a continuous function over an indicated pressure range that includes the threshold pressure, with the second pressure reading being different from the first pressure reading when the first pressure reading is substantially equal to the predetermined pressure threshold.

In yet another exemplary embodiment, a method comprises producing a first reading of a quantifiable physical property with a first sensor. The method further comprises producing a second reading of the quantifiable physical property with a second sensor. The method still further comprises indicating a magnitude of the physical property responsively to only the first reading over a first range of the physical quantity. The method yet further comprises indicating a magnitude of the physical property responsively to only the second reading over a second range of the physical quantity that adjoins the first range at a transition magnitude of the physical property. The method further comprises adjusting the indicated magnitude of the physical property in at least one of the first or second regions so that the indicated magnitude does not change abruptly in transitioning between the first and second ranges, the first and second readings being different at the transition magnitude.

BRIEF DESCRIPTION OF THE DRAWINGS

The exemplary embodiments are explained in the following description, taken in connection with the accompanying drawings, wherein.

DETAILED DESCRIPTION OF THE EXEMPLARY EMBODIMENT(S)

Figure 1:
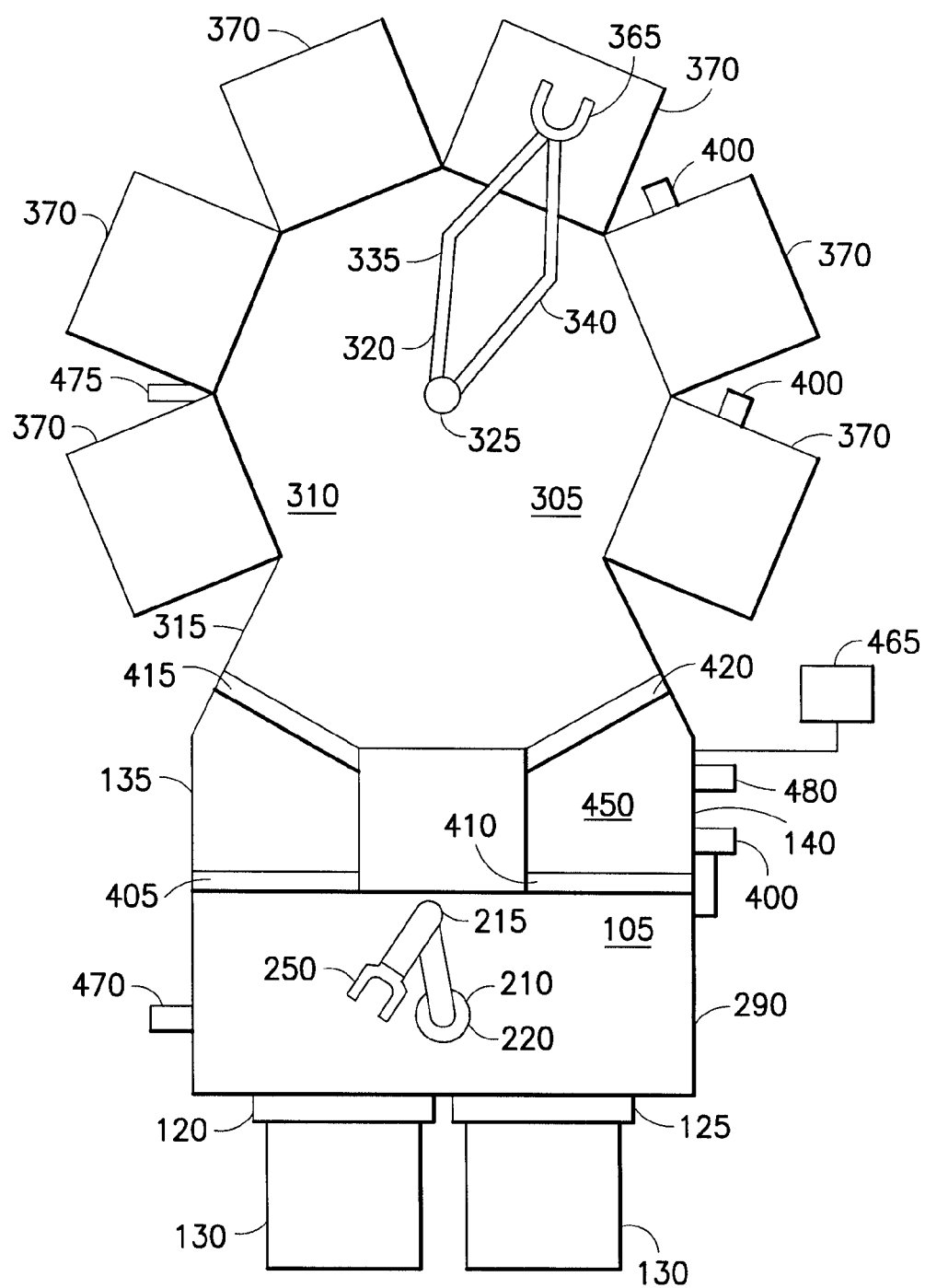
FIG. 1 is a top schematic view of a substrate processing apparatus incorporating an exemplary embodiment of a measurement instrument.

FIG. 1 illustrates an exemplary substrate processing apparatus 100. The apparatus may have an exemplary embodiment of a pressure measurement instrument 400, as further described below. The substrate processing apparatus is described as an example application of the pressure measurement instrument 400. It should be understood that the pressure measurement instrument may be used in any suitable application, such as to measure a pressure or gas density within any suitable pressure or vacuum chamber, or may operate independently of any pressure or vacuum chamber. Although the exemplary embodiments will be described with reference to the embodiments shown in the drawings and described below, it should be understood that these aspects could be embodied in many alternate forms of embodiments. In addition, any suitable size, shape, or type of elements or materials could be used. In FIG. 1, the apparatus 100 may, for convenience, be described as having a front end 200 and a back end 300. The front end 200 may have a frame 230 and may comprise a substrate transport apparatus 210 operating within, for example, a controlled environment 105. Transport apparatus 210 may have an arm 215 and a drive mechanism 220 that is operable to move the arm. The arm 215 may have an end effector 250 for supporting a substrate.

The front end 200 of the example apparatus 100 may also include load ports 120,125 (two are shown for example purposes). The load ports provide an interface with substrate cassettes 130. Each substrate cassette is adapted to hold several substrates, and may hold them within a sealed enclosure. The load ports 120,125 removably hold the cassettes 130 and may include mechanisms (not shown) to open cassette doors, allowing access to the substrates located in the cassettes from within a controlled environment 105 of the front end 200. The controlled environment 105 may be contained by a housing, and may be connected to a pressure gauge 470 for measuring pressure of the controlled environment 105. Opposite the transport apparatus 210 from the load ports 120,125 are load locks 135,140. Load locks 135,140 connect the front end 200 to the back end 300. Each load lock 135, 140 has a valve 405, 410 connecting it to the controlled environment 105 of the front end 200 and another valve 415, 420 connecting it to the isolated environment 310 contained in the transport chamber 305 of the back end 300. The isolated environment 310 of the transport chamber 305 may, for example, be a vacuum, inert gas such as nitrogen, or other fluid. The controlled environment 105 of the front end 200 may be clean air at atmospheric pressure, maintained with very low levels of particulate contaminants. Thus, the load locks 135,140 allow passage of substrates between the front end 200 and the back end 300 while maintaining isolation of the two environments 105, 310. In FIG. 1, load lock 140 is shown connected to both an inlet valve 480 for pressurizing the load lock, and a vacuum pump 465 for depressurizing the load lock.

In the example apparatus 100, back end 300 comprises a frame 315 defining a transport chamber 305. As noted above, the transport chamber 305 may hold an isolated environment 310, such as a vacuum. A pressure gauge 475 may be connected to the transport chamber 305 for reading pressure of the isolated environment 310. A substrate transport apparatus 320 may be located within the transport chamber 305. Transport apparatus 320 may comprise a drive mechanism 325 connected to the frame 315 and a pair of opposing arms 335,340 connected to an end effector 365.

In the example apparatus 100 of FIG. 1, several processing modules 370 are located on the periphery of the transport chamber 305. The processing modules 370 may operate on the substrates through various deposition, etching, polishing, cleaning or other types of processes to form electrical circuitry or other desired structure on the substrates, or to perform metrological or other functions. The processing modules 370 are connected to the chamber 305 to allow substrates to be passed from the transport chamber to the processing modules and vice versa. The processing modules, in the exemplary embodiment, may be isolatable from the transport chamber, for example via slot valves or other suitable doors, hence one or more of the processing modules may be capable of holding an atmosphere, such as an inert gas (e.g. nitrogen, argon), that is isolated from the atmosphere or vacuum in the transport chamber 305. One or more of the processing modules may be subjected to varying pressures, such as an operating pressure during workpiece processing (e.g. low vacuum) a loading pressure (e.g. high vacuum during loading/unloading of workpieces) and access pressure (e.g. ambient atmospheric for maintenance of the module). Similarly the transport chamber 305 may also be subjected to different pressures. In the exemplary embodiment one or more of the processing modules may have a pressure gage or measurement instrument 400 capable of measuring the pressure in the processing modules as will be described further below.

Load lock 140 may be connected to a pressure measurement instrument 400 as well. Load lock 135 may also be connected to a similar pressure measurement instrument. The pressure measurement instrument 400 may measure an absolute pressure of an atmosphere 450 within a desired section(s) of the apparatus 100 such as the load lock 140, transport chamber 305 or processing modules. In alternate embodiments, the measurement instrument may measure a relative or differential pressure, or both. In other embodiments, instrument 400 may measure a gas density or other physical characteristic that may serve as a proxy for pressure measurement. In still other embodiments, a measurement instrument may measure any suitable physical characteristics.

Figure 2:
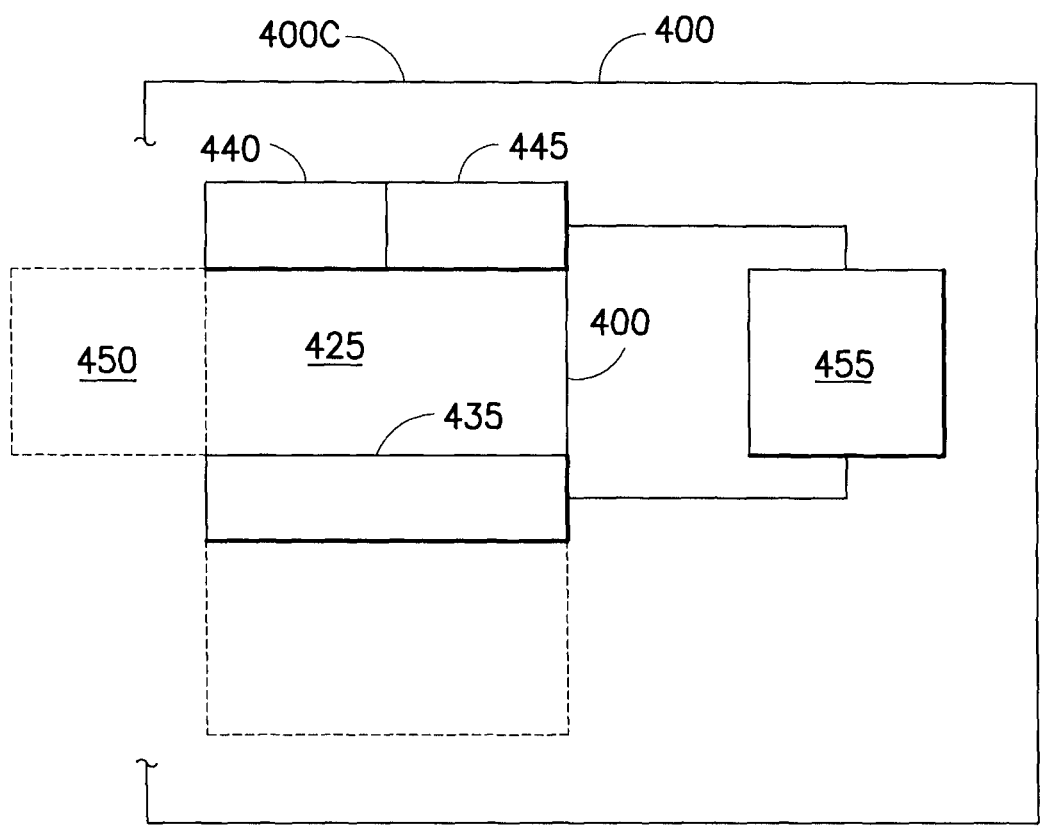
FIG. 2 is a schematic illustration of the exemplary embodiment measurement instrument of FIG. 1.

FIG. 2 is a schematic illustration of the measurement instrument 400 in accordance with an exemplary embodiment. In the exemplary embodiment shown, measurement instrument 400 may be an integrated instrument, housed for example in a casing or housing 400C. Accordingly, in the exemplary embodiment, the measurement instrument 400 may be modularly installed to any one or more of the desired sections of the processing apparatus 100 such as the transport chamber, processing modules or loadlocks for example. In alternate embodiments, the measurement instrument may be installed to measure desired physical characteristics of an atmosphere in any desired apparatus. In other alternate embodiments, the measurement instrument as will be described further below may be integrated within the apparatus or tool holding the atmosphere measured by the instrument. As seen in FIG. 2, in the exemplary embodiment, the casing 400C may be configured to define a pressure envelope 425 in communication with atmosphere 450 that is held within the measured section of apparatus 100, (e.g.) the load lock 140 or process module(s) 370). Hence, pressure within the pressure envelope 425 is substantially the same as pressure within the load lock 140 (loadlock 140 as referenced below is merely a representative section of apparatus 100). In the exemplary embodiment the pressure envelope is depicted as being located within the housing for example purposes only (a port for example may be provided between the interior of the apparatus with atmosphere 450 and the pressure envelope 425 for communication). In alternate embodiments, the pressure envelope of the measurement instrument may be located as desired including exterior to the instrument housing. In the exemplary embodiment shown, three pressure sensors may be connected to the pressure envelope and operable to measure pressure within the envelope. In alternate embodiments more or fewer pressure sensors may be connected to sense the pressure in the pressure envelope. Other alternate embodiments may or may not have a pressure envelope, and may have any suitable number of sensors. In the exemplary embodiment, pressure sensor 435 may comprise a piezo-resistive diaphragm (PRD). One side of the diaphragm may be connected to the pressure envelope 425. Another side of the diaphragm may be sealed off at high vacuum so that the PRD is an absolute diaphragm sensor. The PRD sensor 435 may be operable to detect an absolute pressure of the pressure envelope 425 in pressure envelope 425. For example, a change in pressure may cause a stress or change in stress or strain within the piezo resistive diaphragm that affects the resistivity of the diaphragm. The sensor 435 may hence, sense a pressure or change in the pressure in envelope 425 by measuring a change in electrical resistance in the diaphragm. Sensor 440 may also be connected to the pressure envelope 425. Sensor 440 may be, for example, a heat loss sensor. Heat loss sensor 440 may be operable to sense an absolute pressure within the pressure envelope 425 by sensing heat loss from an electrical conductor. The heat loss may correspond to the pressure within the pressure envelope 425, and hence for example within the load lock 140. Sensor 445 may also be connected to the pressure envelope 425. Sensor 445 may be, for example, an ionization sensor. The ionization sensor 445 may emit electrons that collide with gas particles in the measured gas. The collisions may create ions that conduct an electrical current. The amount of current may correspond to gas density and gas pressure within the pressure envelope 425, and hence may correspond to pressure within the load lock 140.

In the exemplary embodiment, each of the sensors 435, 440, 445 may have a different operating pressure range. For example, a high vacuum (e.g. $10^{-10}$ Torr to $10^{-2}$ Torr) may be most accurately measured by the ionization gauge (IG) 445. A medium vacuum (e.g. $10^{-3}$ to 1000 Torr) may be most accurately measured by the heat loss (HL) sensor. The PRD sensor 435 may be used for measuring low vacuum to atmospheric pressure as illustrated substantially in FIG. 2. Instrument 400 may include a signal processor 455 that is communicably connected to the respective sensors 435, 440, 445. In general, the signal processor is capable of receiving the sensor signals and converting them to output a desired measurement signal. As may be realized, the measurement instrument 400 may be used to measure transient and steady state pressure, within one or more desired chambers or modules of the processing apparatus 100, that may range from atmospheric to high vacuum (e.g. 13 decades). The processor 455 is capable of using the signals from the sensors 435, 440, 445 to generate the output measurement signal indicating the measured pressure (or other measured characteristic) in the range from about $10^{-10}$ Torr to about 1000 Torr as will be described below.

Figure 3:
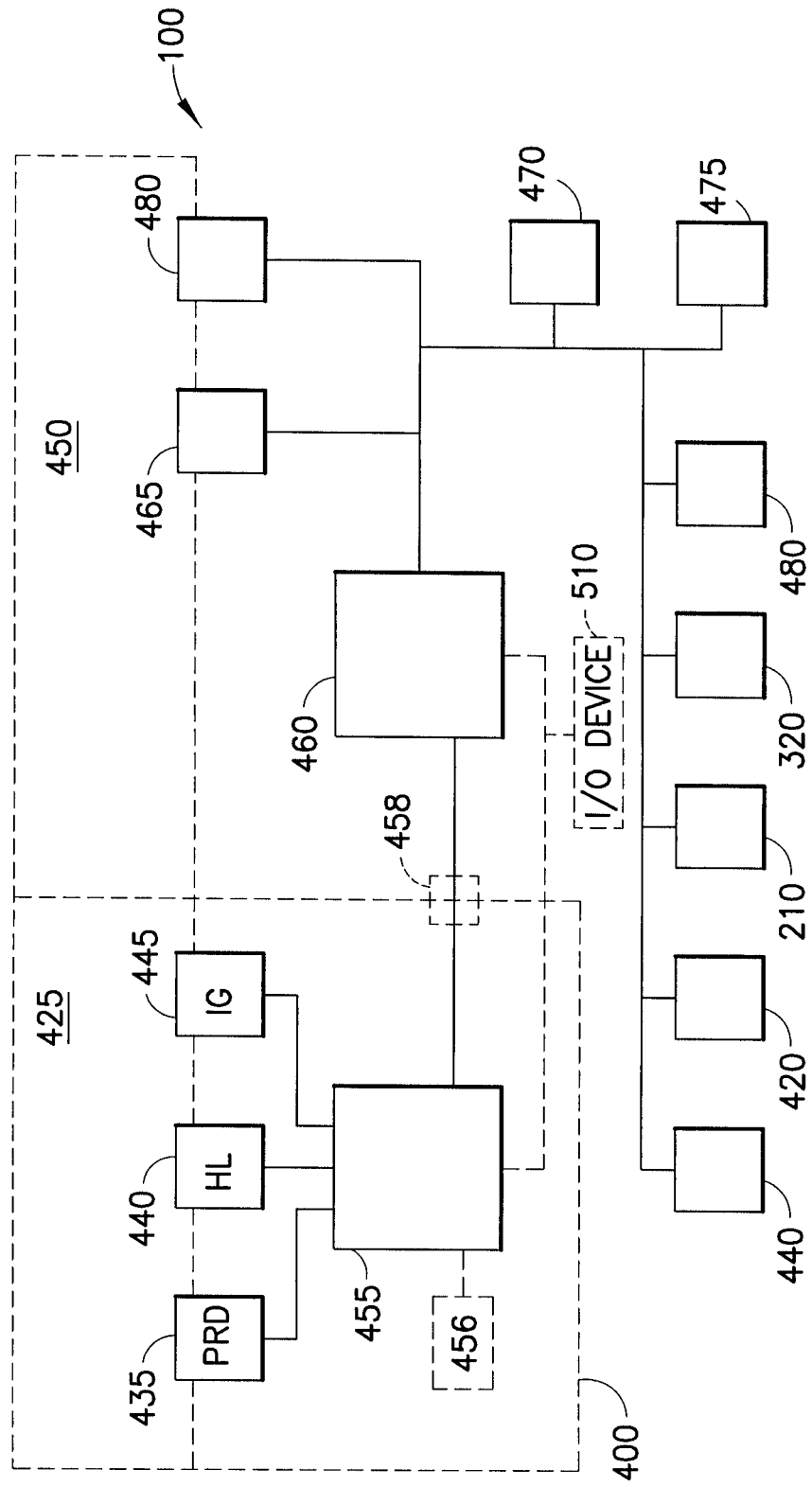
FIG. 3 is a system diagram illustrating connectivity between various parts of the processing apparatus of FIG. 1.

FIG. 3 illustrates schematically various connections of the measurement instrument 400 to the substrate processing apparatus 100. As noted previously, the measurement instrument in the exemplary embodiment (see also FIG. 2) may be an integrated package that may be modularly installed or removed from the apparatus 100. The measurement instrument module may be mechanically connected to the desired sections of the apparatus 100 (e.g. transport chamber 325, process modules 370, load lock(s) 135, 140) so that the pressure envelope 425 of the instrument module is in communication with the desired atmosphere 450 within the apparatus. For example, the instrument housing 400C may be attached to the frame of apparatus 100 by suitable fasteners (e.g. screws, quick release clamps, etc.). The instrument module 400 may also be electrically connected, for example via a wired (e.g. USB) or wireless coupling 458, to the apparatus 100 for power and communication. The signal processor 455 may be connected via coupling 458 to a control system 460 of the apparatus 100. In the exemplary embodiment, the signal processor may be operable to generate an output measurement signal, using multiple readings from the sensors 435, 440, and 445, that is communicated to the control system 460. In the exemplary embodiment, the control system 460 may also be connected to other devices of the processing apparatus 100, such as the substrate transport apparatus 210 and 320. The control system may also be connected, for example, to the load ports 135, 140 processing modules 370, any other suitable devices of the apparatus 100 and any devices external to the apparatus 100. The control system 460 may be connected to a vacuum pump or system 465 for regulating pressure within the transport chamber 305, modules and load lock(s) 140 of the apparatus. In the exemplary embodiment, the control system may also be connected to an absolute pressure sensor 470 for monitoring pressure within the controlled atmosphere 105 of the front end 200. The control system 460 may be connected to a vent valve 480 for venting load lock 140, and may be connected to loading valves 410, 420 of the load locks and process modules. Thus, the control system 460 may be operable to coordinate operations of the apparatus 100, such as transport of substrates through the load locks 135, 140 and other process modules. Processor 455, of the instrument module, and/or control system 460 may also be directly or remotely connected to a suitable I/O device 510 (see FIG. 3) that is capable of inputting information to control system 460 and processor 455, and also capable of displaying information, such as the indicated pressure measurement (or other measured characteristic) output from the processor 455.

In one example operation of the processing apparatus 100, a substrate may be removed by transport apparatus 210 from a substrate cassette 130 docked at load port 125. Pressure sensor 470 may measure pressure within the controlled environment 105 and communicate the measured pressure to control system 460. The control system 460 may also identify and monitor the operating status of the desired sections of apparatus 100. For example control system 460 may determine or confirm whether the desired pressure or vacuum condition is present in the transport chamber 305 and process modules using measurement instrument 400. As may be realized, in the event conditions do not conform to desired protocol, the control system may generate a fault signal and may for example initiate (automatically or with operator input) remedial procedures. By way of example, if the control system registers from the output of measurement instrument 400, that the transport chamber is not at a desired vacuum condition, the control system may activate vacuum pumps to establish desired vacuum. Upon receiving indication from measurement instrument 400 that desired vacuum has been established in the transport chamber 305, the control system may automatically deactivate the vacuum pump. Generation or maintenance of desired atmospheric condition may be similarly effected in any desired section or module of the apparatus 100. The control system 460 may also determine the status of and control the operation of load lock(s) 135, 140 using the measurement instrument connected to the load ports. By way of example, the measurement instrument 400 may measure pressure within the load lock 140 using the pressure sensors 435, 440, and 445, and send an indication (from the signal processor 455) of the measurement to the control system 460. The control system may compare pressure measurement indications between load lock 140 and control environment, and operate the vacuum pump 465 to control the pressure within the load lock 140 so as to equalize pressure between the load lock atmosphere 450 and controlled environment 105. Both valves 410, 420 of the load lock 140 may be sealed as the pressure is equalized. In equalizing the pressure, the control system may use the unified output from the signal processor 455 to provide a feedback signal for controlling the vacuum pump 465. As noted before, and as will also be described in greater detail below, the pressure variance in the load lock 140 (e.g. between matching atmospheres with the transport chamber and the environmental front end), or any other desired chamber of the apparatus, may be such (e.g. decades) that the measurement range of each sensor 435, 440, 445 may not be sufficient to accurately measure pressure across the whole pressure variance. Thus the pressure indication from the measurement instrument measuring the pressure in the load lock may be based on two or more of the sensors 435, 440, 445. For example the pressure indicated by the instrument when the load lock, or any other chamber/module, is at high vacuum may be based on the IG sensor 445, at low vacuum the indication may be based on the HL sensor 440, at atmospheric pressure the indication may be based on the PRD sensor 435. As may be realized from FIGS. 1 and 3, valve 410 between the load lock 140 and controlled environment 105 may be opened by control system 460 upon receiving a suitable pressure indication from the processor 455 allowing the control system to determine that pressures across valve 400 are balanced. The pressure indication from sensor may also be displayed on I/O device 510 (see FIG. 3). Because pressure between the load lock atmosphere 450 and controlled environment 105 is substantially equal, there may be no rush of gas upon opening of the valve 410, which could cause dispersal of contaminants onto the substrate. The control system 460 may then direct the substrate transport apparatus 210 to transfer substrate(s) between the load lock 140 and front end. Upon completion of substrate transfer, the valve 410 may be closed, leaving the load lock atmosphere sealed off from the controlled environment 105 of the front end, as well as from the isolated environment 310 of the back end 300. The control system may equalize pressure between the load lock atmosphere 450 and the isolated environment 310 by pumping down the pressure within the load lock using the vacuum pump 465. The measurement instrument 400 may provide a feedback signal to the control system 460, which may be used in controlling the vacuum pump 465. The control system may also monitor pressure within the isolated environment 310 using pressure sensor 475. When the control system has determined that pressure is substantially balanced between the load lock atmosphere 450 and isolated environment 310 of the transport chamber 305, the control system may open the valve between the load lock 140 and the transport chamber 305 for substrate transfer between the load lock and transport chamber. This process may be repeated as desired for loading and unloading substrates between the front and back ends of the apparatus 100. Similarly, the measurement instruments 400, mounted on one or more of the process modules and the transport chamber, may facilitate loading/unloading of substrates between transport chamber and process module(s) isolated from the transport chamber during processing. As may be realized, the example operations described above merely serve to illustrate applications of the exemplary embodiment measurement instrument 400. The measurement instrument 400 may be used in any suitable application, such as any suitable application wherein a pressure or density of a gas is measured. In alternate embodiments, the measurement instrument may measure any suitable physical quantity or quantities.

Figure 6:
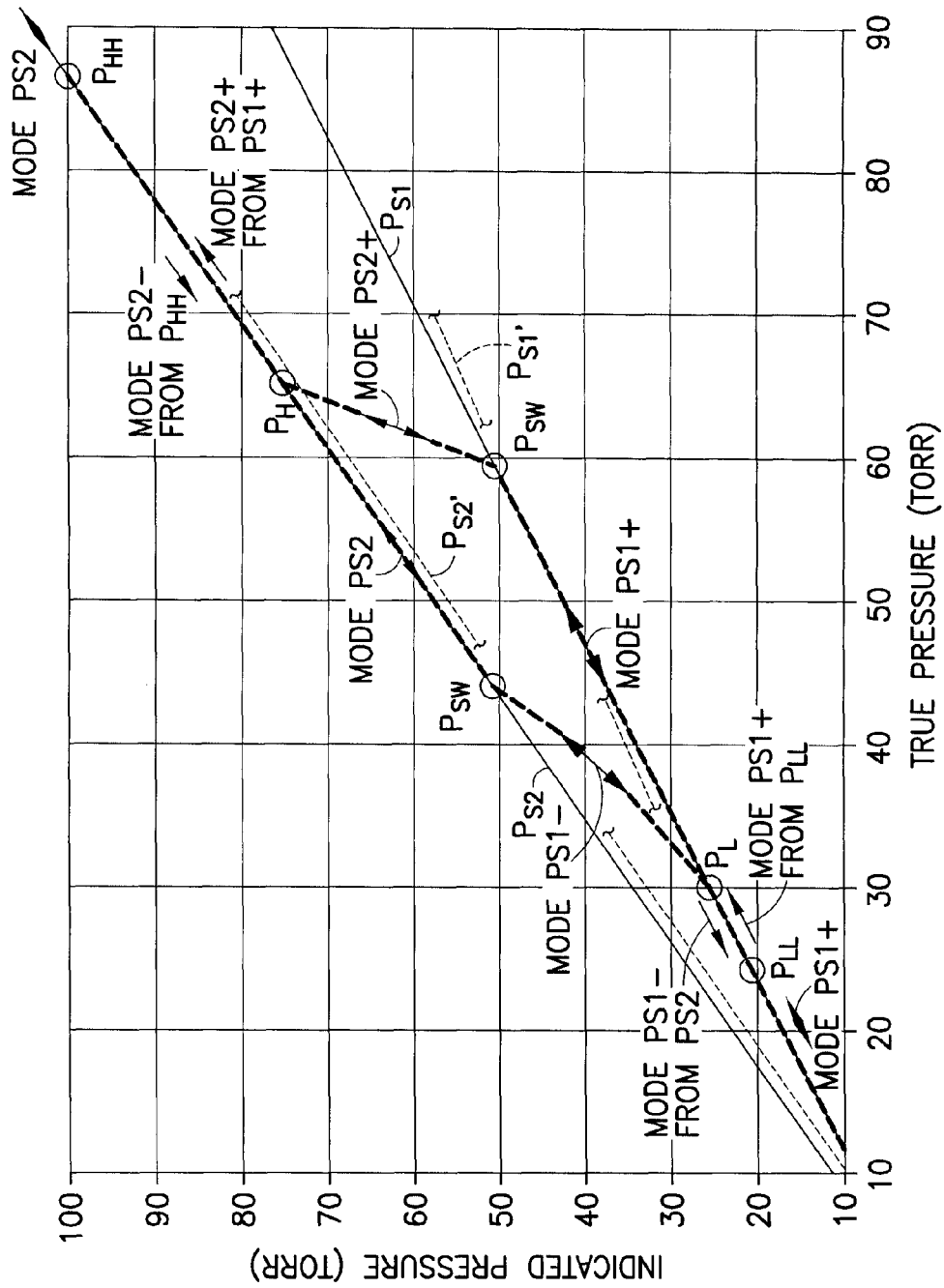
FIG. 6 is another signal diagram corresponding to the exemplary embodiment.

As noted before, in the exemplary embodiment, the pressure instrument 400 may be arranged to measure pressures throughout the full pressure variance (e.g. 13 decades; from $10^{-10}$ to $10^{-3}$ Torr) in the desired chamber/module using the three sensors 435, 440, 445 (though in alternate embodiments, depending on the extent of the pressure change in the chamber, more or fewer sensors may be used). As also noted before, in the exemplary embodiment, each sensor 435, 440, 445 may have a different pressure range, the different pressure ranges of the three sensors being used together to provide instrument 400 with the desired overall measurement range. The processor 455 (see FIGS. 2-3) may be programmed, in the exemplary embodiment, so that its measured pressure output (i.e. indicated pressure from the instrument) is based on the best data from the sensors 435, 440, 445. Accordingly, in the exemplary embodiment, at a given pressure, the processor 445 programming uses the measurement data from the sensor with the greatest accuracy (i.e. best data) for the given pressure as will be described below. In the exemplary embodiment, the pressure range of each sensor 435, 440, 445, or in other words the range of pressure where each sensor has the greatest accuracy relative to the other sensors of the instrument may be programmed in processor 455. By way of example, the processor 455 (or a suitable memory location accessible by processor 455) may have programming 456 such as a suitable algorithm or lookup table to identify and select the pressure range for each sensor. For example, the processor may directly or indirectly use the calibration line relating indicated pressure (e.g. output signal as a function of true pressure) from each sensor with true pressure to establish the gage pressure range. The calibration information for each particular sensor 435, 440, 445 may be downloaded, for example over a global or local network(s), or otherwise entered in any other suitable manner into the processor 455. In alternate embodiments, the sensor calibration information may be stored at a remote location (for example a PC at the instrument manufacturer facility) and accessed as desired by the processor via a suitable bi-directional communication path. In other alternate embodiments, the calibration information may be generated by the processor 455, with the instrument mounted in place and using known sensor calibration techniques. FIG. 6 graphically illustrates representative calibration lines (e.g. gain) PS1, PS2 for two sensors 435, 440, 445. As may be realized, the calibration plots or lines for some of the different types of sensors (e.g. IG sensor 445 or HL sensor 440) may vary for different gas species (e.g. controlled air, $N_2$, argon). In the exemplary embodiment, the programming of processor 455 may be arranged to effect selection of the sensor calibration information corresponding to the gas species expected to be measured in the chamber. For example, the calibration lines of each sensor for different gas species may be stored in program 456 of processor 455. The processor program 456 may correlate the respective calibration lines to the corresponding gas species for each sensor, and select the appropriate calibration line upon receiving an input, such as from the I/O device 510 or any other desired means, identifying the gas species in the chamber the pressure of which is to be measured with instrument 400. In alternate embodiments, the processor 455 may read or download the appropriate calibration line from the remote location after receiving the input identifying the gas species in the chamber.

As may also be realized, for sensors of a given type (e.g. IG, HL or PRD), the calibration lines may also vary from sensor to sensor. The calibration lines PS1, PS1' and PS2, PS2' shown in FIG. 6 graphically illustrate the variance that may exist in calibration lines or gain for different sensors of the same type. As noted before the plots shown in FIG. 6 are merely exemplary. In the example shown, lines PS2, PS2' may correspond to different PRD sensors and lines PS1, PS1' may correspond to different HL sensors. Lines PS2, PS1 may correspond to PRD and HL sensors 435, 440 of instrument 400 respectively. The characteristics of the lines PS1, PS1', PS2, PS2' are merely exemplary and in alternate embodiments the calibration lines of the sensors may have any other desired characteristics. The calibration lines PS2, PS2' for the different PRD sensor(s) are shown for example only as having a relatively higher gain than the calibration lines PS1, PS1' marking the performance of the different HL sensors. In alternate embodiments, the relative gains for the different types of sensors may be different. The calibration lines for the IG sensor (not shown) may have generally similar characteristics to the calibration lines shown in FIG. 6, and the relationship between calibration lines of the IG sensor (such as sensor 445) and HL sensor (such as sensor 440) may be for example generally similar to that shown for the calibration lines PS2, PS2', PS1, PS1' in FIG. 6. In one exemplary embodiment, the processor 455 may be programmed to calculate or otherwise identify for example, from the calibration line PS1, PS1', PS2, PS2' of the corresponding sensors 435, 440, 445 for the given gas species the pressure (or other measured characteristic) range where each sensor provides the best data. By way of example, the calibration lines of the specific sensors 435, 440, 445 (of instrument 400) for the gas species registered by the processor (as noted before) may be compared to desired thresholds to establish the best data pressure ranges (or what shall be referred to hereafter as the pressure range) of each sensor 435, 440, 445 for the given gas species. In alternate exemplary embodiments, the pressure ranges of the sensors may be entered into or downloaded by the processor from a remote location. As may be realized from the above, the pressure range registered in the processor may be sensor specific and species specific. By way of example, the processor programming 456 may include information (such as an algorithm or table) that defines range information for each sensor 435, 440, 445 corresponding to the various gas species. As noted before, with the pressure range of each sensor 435, 440, 445 registered by the processor, the processor 455 in the exemplary embodiment may use the pressure reading from the sensor(s) with the appropriate pressure range as the sensors measure the pressure change in the chamber. Moreover, as may be realized in the exemplary embodiment the processor 455 may transition between sensors when the pressure(s) measured exceed the pressure range of the given sensor.

In order to prevent gaps in the instrument 400 measurement range, the pressure ranges for the sensors 435, 440, 445 may be established to provide desired overlap. Thus for example the pressure range for PRD sensor 435 may overlap the pressure range of the HL sensor 440, which in turn may overlap the pressure range of the IG sensor 445. A representative overlap region between two sensors 435, 440, 445 is graphically illustrated in FIG. 4a that shows lines 501, 502 depicting sensor readings for the sensors within the corresponding sensor pressure ranges. As may be realized, the sensor performance lines 501, 502 in FIG. 4a (i.e. relating sensor readings to true pressure for the respective sensors) are substantially similar to portion(s) of the sensor calibration lines PS1, PS2 shown in FIG. 6. Further, in the exemplary embodiment lines 501, 502 may also represent the indicated pressure ($P_{ind}$) from the processor (relative to true pressure). Hence, and as will be described in greater detail below, in the exemplary embodiment, the indicated pressure from processor 455 may be a function of the present value (i.e. pressure reading) of but one sensor 435, 440, 445 even in the overlap region. Accordingly, as may be realized from FIG. 4a, the amount of overlap can be minimized and be much smaller than range overlap desired with conventional systems. For example, and as will also be described further below, the overlap may be so that when one sensor 435, 440, 445 is at the end of its range, the reading from the other sensor is valid hence allowing the processor to switch between sensors. However, as noted before the sensor pressure range, and hence the end points of the range may vary between gages (of the same type) as well as between gas species. In the exemplary embodiment, the processor may be arranged to select or allow selection of the end point(s) of the pressure range for the sensors, and hence selection of the switch pressure ($P_{ind}$) where the processor switches between sensors, for example so that the pressure indication from the instrument 400 may be based on best data using the current pressure reading (value) from but one sensor 435, 440, 445. In alternate embodiments, the switch pressure (Psw), where the pressure indication switches sensors, may be entered into the processor by the operator, for example via the I/O device 510 (see FIG. 3), or maybe downloaded by the processor from a remote location.

Figure 4A:
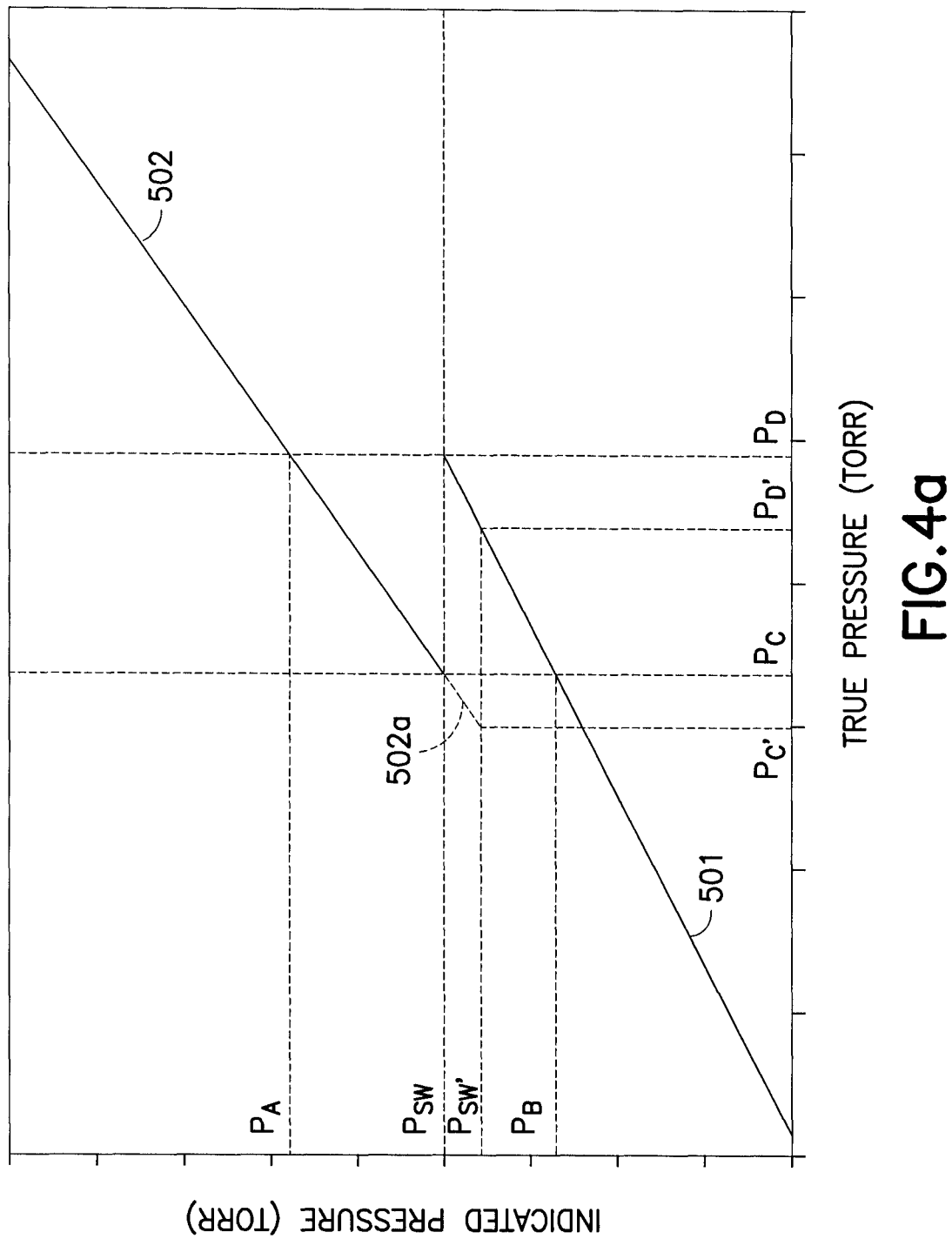
FIG. 4a is a signal diagram illustrating sensor signals in the exemplary embodiment.

Referring again to FIG. 4a, which illustrates, as noted before, an example of how pressure readings from two sensors may vary with respect to a true pressure. In FIG. 4a, line 501 may represent, for example, a pressure reading from ionization sensor 445. Line 502 may, for example, represent a pressure reading from heat loss sensor 440. As described above heat loss sensor 440 and ionization sensor 445 may have different operating ranges. Therefore it may be desired to use a pressure reading from ionization sensor 445 at pressures below a switching pressure $P_{SW}$ as a basis for an indicated pressure from the instrument 400, and use a pressure reading from heat loss sensor 440 as a basis for the indicated pressure at pressures above the threshold pressure $P_{SW}$. As seen best in FIG. 4a, there is a variance between the readings from the two sensors (see also FIG. 6). Thus, as the sensors 440, 445 may not produce identical pressure readings at the threshold pressure $P_{SW}$, switching between the two sensor readings at the switching pressure would result in an abrupt jump or discontinuity in the indicated pressure from the instrument. The presence of discontinuities in a data stream that may be subjected to some kind of processing are highly undesired. For example, differentiating an indicated pressure at or near the threshold pressure $P_{SW}$ might then result in a high magnitude value for rate of change in pressure, which could introduce hysteresis in a pressure control feedback system or generate faults in the processing system. For example, when monitoring an environment of decreasing pressure, a reading from heat loss sensor 440 may first be used to determine the indicated pressure $P_{IND}$. This would follow line 502. When a reading from heat loss sensor 440 reaches the threshold pressure $P_{SW}$, a reading from the ionization sensor 445 may then be used to determine the indicated pressure $P_{IND}$. This would follow line 501. However, as exemplified in FIG. 4a, when heat loss sensor 440 is reading the pressure as equal to $P_{SW}$, the true pressure would be $P_C$ and ionization sensor 445 would read a pressure of $P_B$. As $P_B$ does not equal $P_{SW}$, a sharp change in the indicated pressure $P_{IND}$ would occur. This sharp change in pressure would not reflect the change in true physical pressure, but would merely be an artifact introduced by the measurement instrument. A similar phenomenon may occur in a rising pressure environment, where $P_{IND}$ first follows the line 501 readings of sensor 445, and then shifts to follow the line 502 readings of sensor 440. When a reading from sensor 445 reaches the threshold pressure $P_{SW}$, true pressure would be $P_D$ and the pressure reading of sensor 440 would be $P_A$. As $P_A$ is a different value than $P_{SW}$, merely switching from one sensor reading to another may create a sharp jump or a discontinuity in the indicated pressure $P_{IND}$.

Figure 4B:
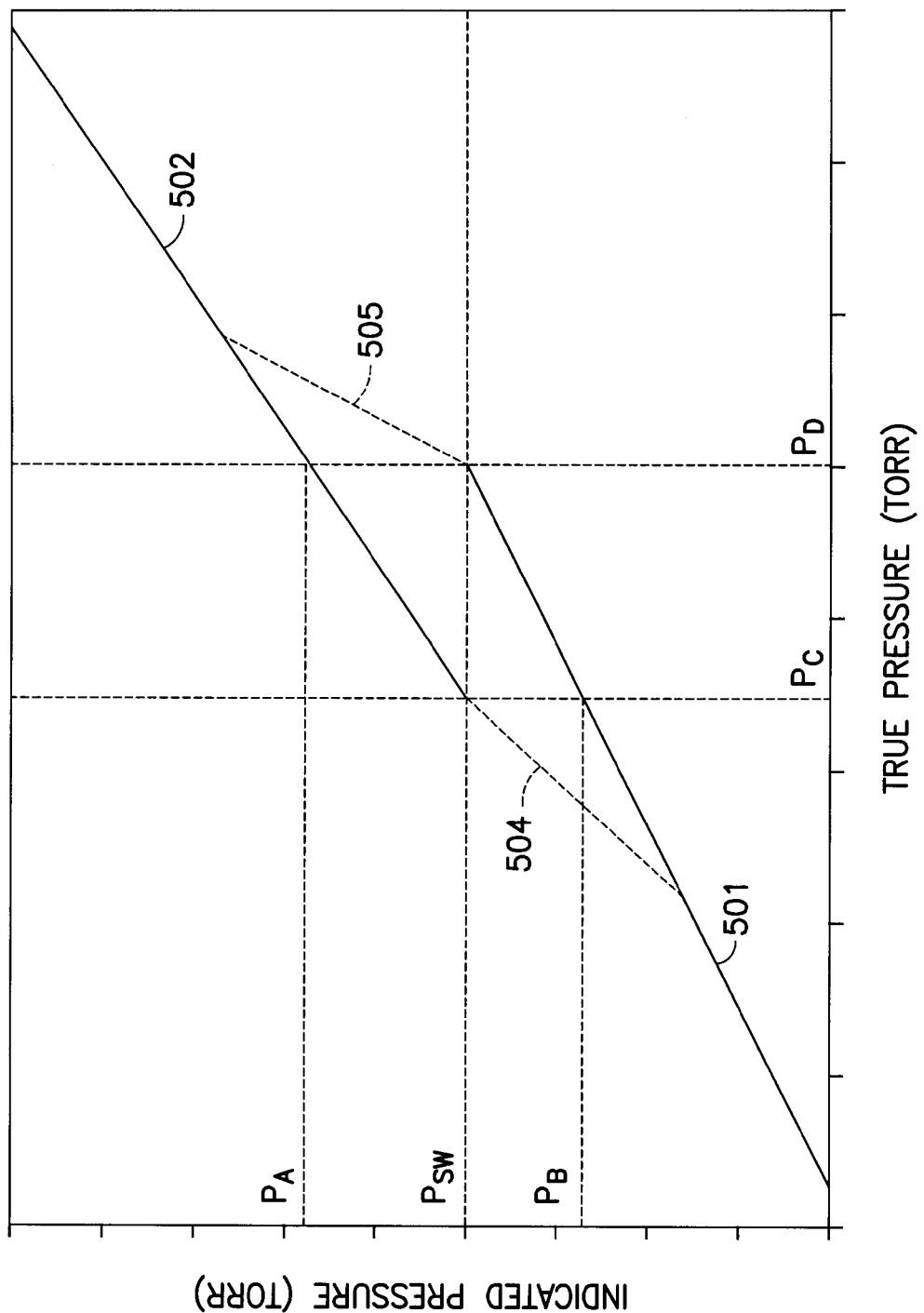
FIG. 4b is another signal diagram illustrating sensor signals in the exemplary embodiment.

As shown in FIG. 4b, the indicated pressure $P_{IND}$ may be adjusted over some range to gradually transition the difference in pressure readings of two sensors when the processor is switching from a reading of one sensor to another sensor. In the exemplary embodiment in the transition, the signal processor 455 may use the prior pressure readings from what may be referred to for purposes of description as the "switching from"=sensor (e.g. the sensor the processor is switching from) to adjust the current reading from the "switching to" sensor (e.g. the sensor the processor is switching to in order) to produce the output signal. FIG. 4b shows, in one example, how the output signal $P_{IND}$ may vary with respect to the true pressure in transition between sensors. As may be seen, when true pressure is relatively high and is falling, the indicated pressure $P_{IND}$ may correspond directly to, and be substantially equal to, the reading from heat loss sensor 440, and therefore may follow line 502. When the pressure reading from sensor 440 falls below threshold pressure $P_{SW}$, $P_{IND}$ then may become determined by a reading from sensor 445. However, $P_{IND}$ is adjusted relative to the reading from sensor 445 (the "switching to" sensor) to compensate for the differences in readings from the two sensors at the point where $P_{IND}$ is switched from being determined by the sensor 440 (the "switching from" sensor) reading to being determined by the sensor 445 reading. Thus, $P_{IND}$ follows along curve 504 as the true pressure continues to drop. At some point, curve 504 and line 501 meet, and $P_{IND}$ is equal to the pressure reading of sensor 445. Below this pressure, $P_{IND}$ may correspond directly to, and be substantially equal to, the reading of sensor 445. In the exemplary embodiment there may not be any time at which $P_{IND}$ is determined from the current readings of both sensors 435, 440, 445. Rather, the indicated pressure $P_{IND}$ may be determined from only one sensor reading throughout the cumulative pressure range of the instrument 400. FIG. 4b also shows curve 505 which may represent transition of $P_{IND}$ in a rising pressure environment. When pressure is relatively low and rising, $P_{IND}$ may be determined from and may be substantially equal to a pressure reading from sensor 445, until $P_{IND}$ reaches $P_{SW}$ and the processor switches for example from sensor 445 to sensor 440). Then $P_{IND}$ may follow transition curve 505 as the pressure continues to rise, and may be determined by a current pressure reading of sensor 440. While following curve 505, $P_{IND}$ be an adjusted value relative the reading of sensor 440. This may prevent an abrupt change in the value of $P_{IND}$ when transitioning from a state in which $P_{IND}$ is determined from sensor 445 to another state in which $P_{IND}$ is determined from sensor 440. As the pressure continues to rise, curve 505 meets line 502, and $P_{IND}$ is equal to a reading of sensor 440. For higher pressures, $P_{IND}$ may correspond directly to, and may be substantially equal to, a pressure reading of sensor 440.

Figure 5:
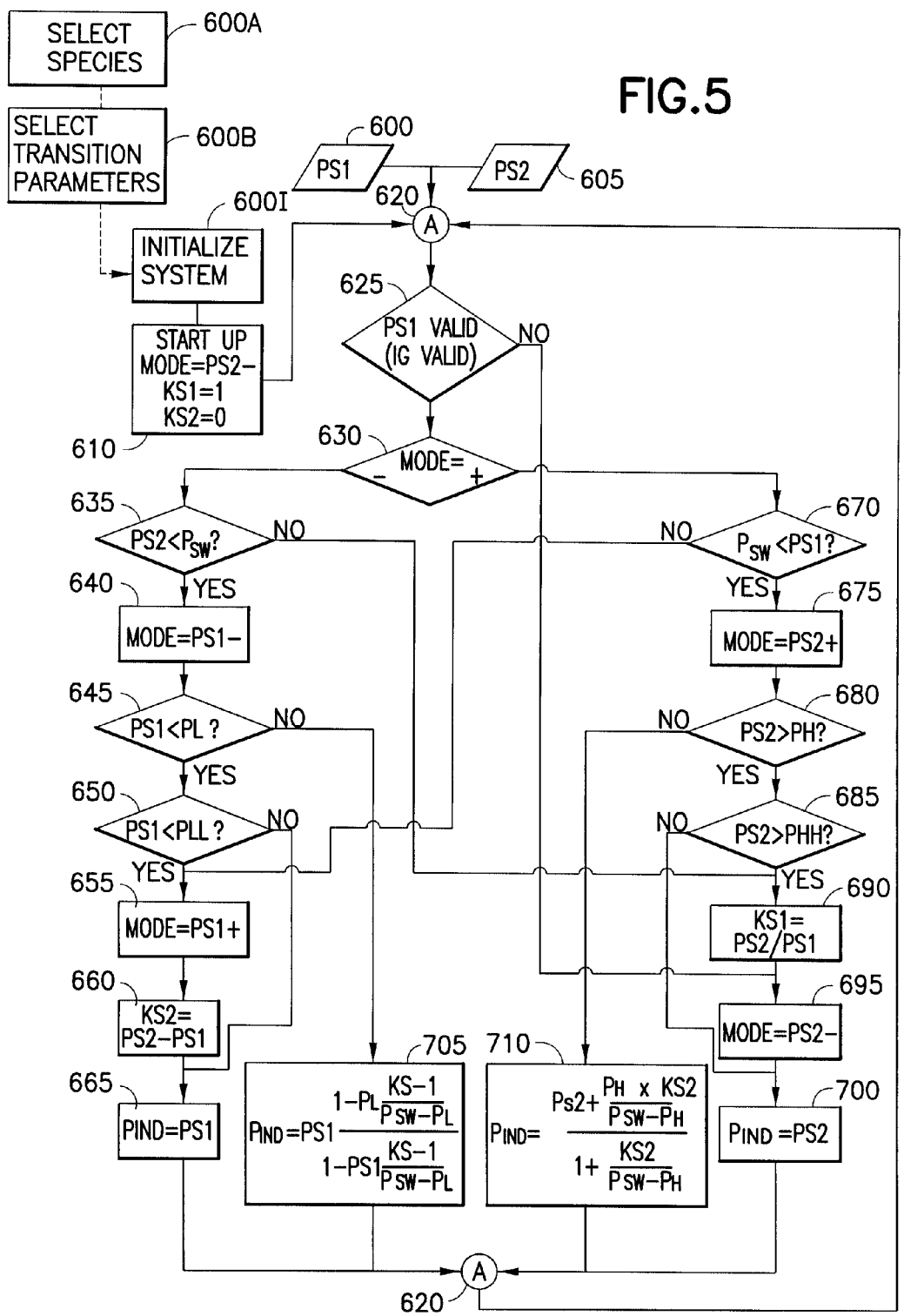
FIG. 5 is a flow chart corresponding to the exemplary embodiment.

FIG. 5 is a flow chart that illustrates one exemplar of the processing performed by the signal processor 455 in generating the indicated pressure, such as of a chamber of apparatus 100, from the pressure readings of the instrument sensors 435, 440, 445. Example results produced by operating the signal processor 455 according to the flow chart are shown in FIG. 6. In the exemplary embodiment illustrated in FIG. 5, blocks 600 and 605, labeled PS1 and PS2, may represent the pressure reading PS1 (described before, see also FIG. 6) from one of the sensors, such as from the heat loss pressure sensor 440. Pressure reading PS2 (also described before) may be a pressure reading from another of the sensors, such as from the piezo-resistive diaphragm pressure sensor 435. Similarly, PS2 and PS1 may be the respective readings from the HL and IG sensors 440, 445. In block 600I, the system may be initialized. As may be realized, system initialization may be performed at any time such as at startup/booting of the processor 455 of instrument 400. For example, the processor may perform a desired initialization routine that may confirm proper operation of the instruments components (including sensors 435, 440, 445). The processor may select the operating parameters such as the respective pressure ranges to be utilized by the processor for the corresponding sensors and the transition points (i.e. $P_{sw}$) where the processor is to switch sensor readings, as well as the program algorithm (or table) to be used to adjust the valve of the corresponding sensor when transitioning between sensors. The processor 455 may select operating parameters for example by registering the gas species block 600A in the chamber (as noted before sensor pressure ranges, and hence transition pressures may vary with gas species). The gas species (e.g. air, N2, argon) may be registered for example by operator input via the I/O device 510 (see FIG. 3) or any other system or device capable of communicating the gas species to the processor. With the gas species registered, the processor may select in block 600B corresponding pressure range of each sensor 435, 440, 445 for the registered gas species. The processor may effect selection for example by accessing a look-up table from internal memory 456 correlating pressure ranges for the sensors with gas species. As noted before, the processor may for example access information correlating or establishing pressure ranges of the sensors for the registered gas specie from remote sensors. In alternate embodiments, the pressure range of each sensor 435, 440, 445 may be selected by the operator entering the respective range for each sensor via the I/O device or any other selector. The transition pressures $P_{sw}$ may be defined by the selection of the pressure ranges for the sensors. For example, as shown in FIGS. 4a, 4b the transition pressure $P_{sw}$ may be set, when the sensor pressure ranges are determined as described previously, to correspond to the ends of the sensor pressure range (e.g. $P_{sw}$ may be set equal to the indicated pressure at the ends, Pc, PD of the sensors pressure range, respectively curved 502, 501). The transition pressures $P_{sw}$ values may be preset and stored for example in the processor memory 456, or in alternate embodiments in any memory location accessible by the processor, so that upon selection of the pressure ranges of the sensors the value of $P_{sw}$ corresponding to the selection becomes identifiable by the processor. In other words the processor is given the value of $P_{sw}$ for the pressure range selection. In alternate embodiments, the processor may be programmed to determine the value of $P_{sw}$ in order to take advantage of the best data from the sensors. As noted before, the accuracy and ranges of different sensors (of the same type) may vary (see for example FIG. 6). Hence, some sensors may have larger ranges, for a given species, than other sensors of the same type. This is illustrated in FIG. 4a by extension line 502a, terminating at end pressure Pc¹, showing an increased range compared to the range of the sensor indicated by line 502. In view of the increased operating range of the sensor, it may be desired to establish the transition pressure identified in FIG. 4a as $P_{sw}'$ to take advantage of the larger range of the sensor and hence set the value of $P_{sw}'$ lower compared to $P_{sw}$ (of a sensor with a smaller pressure range). By way of example, the sensor with the larger range (relative to others of the type) may have some advantage over the one or more of the other sensors 435, 440, 445 of the instrument (e.g. faster response, greater accuracy, reading substantially species independent) and hence it may be desired to employ this sensor over its larger range. By way of example, the PRD sensor 435 may have a quicker response than the HL sensor. Accordingly, it may be desired to use the PRD sensor to the largest extent possible and hence set the switching pressure Psw' (for switching between the PRD and HL sensor) substantially at the limit/end Pc' of the PRD sensor. Hence, the processor 455 may be programmed with the aforementioned selection criteria or factor, setting the value of the switching pressure Psw, Psw', such as between PRD and HL sensors to the lower end of the PRD sensor range, and adjusting the identified pressure range of the HL sensor to end at the pressure Pd' corresponding to the set switching pressure Psw' as noted before, the processor 455 may be programmed with or may be capable of accessing the data for calculating the value Psw, Psw' (e.g. from the identified end points Pc, Pc' and sensor calibration value) and similarly for adjusting the pressure range of the HL sensor. The processor 455 may be programmed with other desired factors for selecting the switching pressure Psw between sensors such as setting the value of the switching pressure to correspond to the sensor with higher accuracy or any other desired selection factors.

Each of the absolute readings PS1, PS2 serve as inputs via block 620. In addition, in block 610 a startup mode is initially set. In block 610, a mode is set to PS2−. The mode is an indication of which sensor reading is currently being used by the processor 455 to determine the indicted pressure $P_{IND}$, as well as whether the pressure is rising or falling. In this example, the pressure is initially high and falling, therefore the mode is set to PS2− to indicate that the $P_{IND}$ should be initially determined from PS2 (i.e. based for example on the PRD sensor rather than the heat loss or ionization sensors), and that the pressure is falling. Also in block 610, the processor may also access the selected transition parameters and set the value of variable KS1 equal to 1 and variable KS2 equal to 0. These variables may be used in connection with the transition parameters to determine $P_{IND}$ in other blocks as described below. In block 625, a determination is made as to whether the PS1 reading is valid (e.g. within the sensor pressure range). In this example, the PS1 reading is determined as valid if it is less than a predetermined value $P_{HH}$. $P_{HH}$ may be an upper endpoint of an operating range of the heat loss sensor 440, above which the heat loss sensor reading PS1 may be insufficiently accurate. In block 630, the current mode is read back to determine whether the pressure is rising or falling. If falling, block 635 is executed. In block 635, PS2 is compared to selected value $P_{SW}$. If PS2 is less than $P_{SW}$, block 640 is executed. Otherwise block 690, described below, is executed. In block 640, the mode is set to PS1− to indicate that $P_{IND}$ is currently responsive to the PS1 reading from the heat loss sensor. In block 645, PS1 is compared to threshold value $P_L$, which is the value of an upper endpoint of a region wherein $P_{IND}$ directly corresponds to the reading PS1 from the heat loss sensor. If PS1 is less than $P_L$, block 650 is executed. Otherwise block 705 is executed to produce a value for $P_{IND}$, as described below. In block 650, PS1 is compared to threshold $P_{LL}$, which may be a lower endpoint of an operating pressure range for the PDR sensor 435, below which the PRD sensor may not be operable to produce a sufficiently accurate reading. If PS1 is less than $P_{LL}$, block 655 is executed. Otherwise, block 665 is executed. In block 665, the mode is set to PS1+ to indicate that $P_{IND}$ is currently responsive to pressure reading PS1 from heat loss sensor 440 and pressure is falling. In block 660, KS2 is set to PS2−PS1. In other words, KS2 is set to the difference between the pressure reading generated from the PRD sensor 435 and the pressure reading from the heat loss sensor 440. In step 665, $P_{IND}$ is set equal to PS1, the reading from the heat loss sensor 440, and block 620 is re-executed.

If at block 630 the mode is determined to be positive, indicating a rising pressure, block 670 is executed. In block 670, PS1 is compared to $P_{SW}$. If $P_{SW}$ is less than PS1, block 675 is executed. Otherwise, block 655 is executed. In block 675, the mode is set to PS2+ indicating that the indicated pressure $P_{IND}$ is responsive to pressure reading PS2 generated with the PRD sensor 435, and that the pressure is rising. In block 680, PS2 is compared to $P_H$, which may be an endpoint of a pressure region within which the indicated pressure $P_{IND}$ corresponds directly to pressure reading PS2 generated with the PRD sensor 435. If PS2 is greater than $P_H$, block 685 is executed. Otherwise, block 710 is executed to generate a value for $P_{IND}$. In block 685, PS2 is compared to $P_{HH}$, which may be an upper endpoint of a range of heat loss sensor 440 above which the sensor 440 is may not be sufficiently accurate. If PS2 is greater than $P_{HH}$, block 690 is executed. Otherwise, block 700 is executed. In block 690, KS1 is set equal to the ratio of PS2 over PS1. In block 695, the mode is set to PS2− to indicate that $P_{IND}$ is responsive to PS2 and is falling. In block 700, $P_{IND}$ is set equal to PS2. Block 620 is then re-executed.

Block 705 is executed when the pressure is falling, reading PS2 generated from the PRD sensor 435 is below threshold value $P_{SW}$, and reading PS1 from the heat loss sensor 440 is above threshold value $P_L$. This is the range wherein $P_{IND}$ is responsive to PS1 and not responsive to PS2, and where $P_{IND}$ is an adjusted value of PS1 with the adjustment smoothing out the $P_{IND}$ curve and avoiding discontinuities, jumps, and high-magnitude differentials. Block 705 defines a value for $P_{IND}$ according to the following formula:

$$P_{IND} = PS1 \frac{1 - P_L \frac{KS1 - 1}{P_{SW} - P_L}}{1 - PS1 \frac{KS1 - 1}{P_{SW} - P_L}}$$

Block 710 is executed when the pressure is rising, reading PS1 generated from the heat loss sensor 440 is above threshold value $P_{SW}$, and reading PS2 generated from the PRD sensor 435 is below threshold value $P_H$. This is the range wherein $P_{IND}$ is responsive to PS2 and not responsive to PS1, and where $P_{IND}$ is an adjusted value of PS2 with the adjustment smoothing out the $P_{IND}$ curve and avoiding discontinuities, jumps, and high-magnitude differentials. Block 710 defines a value for $P_{IND}$ according to the following formula:

$$P_{IND} = \frac{PS2 + \frac{P_H \times KS2}{P_{SW} - P_H}}{1 + \frac{KS2}{P_{SW} - P_H}}$$

Referring again to FIG. 6, there is also shown an example diagram of values for $P_{IND}$ that may result from the process illustrated by the flow chart of FIG. 5. As may be seen, there is no discontinuity in the indicated value $P_{IND}$ at the threshold value $P_{SW}$, regardless of whether pressure is rising or falling. Because there are no abrupt changes in $P_{IND}$ as would occur if P if $P_{IND}$ were simply switched between $P_{IND}$=PS2 and $P_{IND}$=PS1 at the threshold pressure $P_{SW}$, calculating a derivative or slope of $P_{IND}$ at or near threshold value $P_{SW}$ (or elsewhere on the $P_{IND}$ curve) may not result in a value of high magnitude. Therefore it may be possible to use a derivative of $P_{IND}$ as feedback to control pressure, such as for example pressure of load lock atmosphere 450.

As noted above, the exemplary measurement instrument may have an ionization sensor 445 in addition to the PDR sensor 435 and heat loss sensor 440. Readings from all three of the sensors may be used in producing an indicated pressure output operable over an extended range. For example, at pressures below an operating pressure range of the heat loss sensor 440, the indicated pressure may be determined from a reading of ionization sensor 445, which may operate at a lower pressure range than sensor 440. The transition between a state wherein the indicated pressure is determined from the reading of sensor 440 to a state wherein the indicated pressure is determined from the reading of sensor 445 may be handled in substantially similar manner as described previously, with reference to FIGS. 5 and 6, for the transition between using a reading of sensor 435 and using a reading of sensor 440. Thus, the measurement instrument may be operable to indicate pressure across an extended operating range that is inclusive of an operating range of ionization sensor 445 as well as operating ranges of heat loss sensor 440 and PRD sensor 435. Throughout the extended operating range of the measurement instrument 400, an indicated pressure may be always determined from a reading of only one of the sensors, yet the pressure may be indicated without any jumps or discontinuities in indicated pressure created by transitioning from one sensor reading to another. In other embodiments, the measurement instrument may have, for example, two sensors, or may have any other suitable number of sensors. In other embodiments, any suitable physical characteristic may be measured by the sensors and indicated by the instrument (e.g. mass, force, light intensity, magnetic field strength, or other physical quantity or characteristic).

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An apparatus comprising:
at least two sensors each being configured to measure a physical characteristic over respective adjacent measurement ranges where at a transition between the respective adjacent measurement ranges a measurement from one of the at least two sensors is different than a measurement from another of the at least two sensors and the measurement of the physical characteristic is obtained by but one of the at least two sensors during the transition; and
a processor connected to the at least two sensors, the processor being configured to smooth a difference in the measurement of the physical characteristic at the transition between the respective adjacent measurement ranges so that a processor output indication of the measurement from one of the at least two sensors to the measurement from another of the at least two sensors changes gradually.

2. The apparatus of claim 1, wherein the one of the at least two sensors has a first measurement range and the another one of the at least two sensors has a second measurement range adjacent the first measurement range and the processor is configured to adjust the measurement of the physical characteristic relative to the measurement in the second measurement range over at least a portion of the second measurement range so that the measurement of the physical characteristic does not change abruptly when crossing the transition from the first measurement range to the second measurement range.

3. The apparatus of claim 1, wherein the transition is disposed within a predetermined transition range and the respective adjacent measurement ranges partially overlap in the predetermined transition range.

4. The apparatus of claim 1, wherein the physical characteristic is a pressure.

5. The apparatus of claim 1, wherein the physical characteristic is a gas density.

6. The apparatus of claim 1, wherein the processor is further configured to define each respective measurement range based on a gas species registered by the processor.

7. An apparatus comprising:
at least two sensors being configured to sense a physical characteristic and each having a respective measurement range, each of the respective measurement ranges at least partially overlapping in a measurement transition zone where the at least two sensors have different measurements in the measurement transition zone; and
a processor connected to the at least two sensors and configured to
determine each of the respective measurement ranges depending on at least a feature of the physical characteristic,
receive measurement signals of the physical characteristic from the at least two sensors, and
determine the physical characteristic from but one of the at least two sensors in the measurement transition zone with a gradual change in a value of the determined physical characteristic at a switching point from one of the at least two sensors to another of the at least two sensors.

8. The apparatus of claim 7, wherein the processor is further configured to select endpoints of the respective measurement ranges for the at least two sensors where the processor switches between sensors.

9. The apparatus of claim 7, wherein each of the respective measurement ranges depends at least on a characteristic of a respective one of the at least two sensors.

10. The apparatus of claim 7, wherein a measured characteristic of a sensor being switched from is different at the switching point than a measured characteristic of a sensor being switched to and the processor is further configured to adjust a measurement signal from the sensor being switched from relative to a measurement signal from the sensor being switched to for a gradual transition through the difference in the measured characteristic.

11. The apparatus of claim 7, wherein the feature of the physical characteristic is a gas species and the physical characteristic is a pressure.

12. The apparatus of claim 7, wherein the feature of the physical characteristic is a gas species and the physical characteristic is a gas density.

13. A workpiece processing apparatus comprising:
a housing configured to hold an atmosphere therein; and
a measurement instrument connected to the housing and being configured to measure a physical characteristic of the atmosphere, the measurement instrument including at least two sensors each being configured to measure the physical characteristic over respective adjacent measurement ranges where at a transition between the respective adjacent measurement ranges a measurement from one of the at least two sensors is different than a measurement from another of the at least two sensors and the measurement of the physical characteristic is obtained by but one of the at least two sensors during the transition; and
a processor connected to the at least two sensors, the processor being configured to smooth a difference in the measurement of the physical characteristic at the transition between the respective adjacent measurement ranges so that a processor output indication of the measurement from one of the at least two sensors to the measurement from another of the at least two sensors changes gradually.

14. The workpiece processing apparatus of claim 13, wherein the processor is further configured to adjust a measurement signal from the sensor being switched from relative to a measurement signal from the sensor being switched to for a gradual transition through the difference in the measured characteristic.

15. The workpiece processing apparatus of claim 13, wherein the transition is disposed within a predetermined transition range and the respective adjacent measurement ranges partially overlap in the predetermined transition range.

16. The workpiece processing apparatus of claim 13, wherein the physical characteristic is a pressure.

17. The workpiece processing apparatus of claim 13, wherein the physical characteristic is a gas density.

18. The workpiece processing apparatus of claim 13, wherein the processor is further configured to define each respective measurement range based on a gas species registered by the processor.

19. The workpiece processing apparatus of claim 13, wherein the processor is further configured to define each of the respective measurement ranges depending on one or more of a feature of the physical characteristic and a characteristic of a respective one of the at least two sensors.

20. The apparatus of claim 13, wherein the processor is further configured to select endpoints of the respective adjacent measurement ranges for the at least two sensors where the processor switches between sensors.

* * * * *